United States Patent [19]
Riess et al.

[11] Patent Number: 5,904,933
[45] Date of Patent: May 18, 1999

[54] STABLE REVERSE AND MULTIPLE FLUOROCARBON EMULSIONS

[75] Inventors: Jean G. Riess; Marie-Pierre Krafft, both of Nice, France

[73] Assignee: Alliance Pharmaceutical Corp., San Diego, Calif.

[21] Appl. No.: 08/478,824

[22] Filed: Jun. 7, 1995

[30] Foreign Application Priority Data

Jun. 9, 1994 [FR] France .................................. 94 07068

[51] Int. Cl.$^6$ .................................................. A61K 9/127
[52] U.S. Cl. ...................... 424/450; 424/455; 514/832; 514/937; 514/938
[58] Field of Search ................ 424/450, 78.02, 424/455; 514/937, 938, 832

[56] References Cited

U.S. PATENT DOCUMENTS

| | | | |
|---|---|---|---|
| 3,975,512 | 8/1976 | Long | 424/5 |
| 4,917,930 | 4/1990 | McCormick | 424/78 |

FOREIGN PATENT DOCUMENTS

| | | | |
|---|---|---|---|
| 2515198 | 10/1981 | European Pat. Off. | 514/937 |
| 0 250 766 A1 | 1/1988 | European Pat. Off. | 252/312 |
| 0 255 443 A1 | 2/1988 | European Pat. Off. | 514/937 |
| 0307087 | 3/1989 | European Pat. Off. | 252/309 |
| 0 311 473 A1 | 4/1989 | European Pat. Off. | 514/937 |
| 0391637 | 10/1990 | European Pat. Off. | 252/309 |
| 0493677 | 7/1992 | European Pat. Off. | 514/937 |
| 0196904 | 10/1996 | European Pat. Off. | 424/401 |
| 57-109714 | of 1982 | Japan . | |
| WO 90/15807 | 12/1990 | WIPO | 514/937 |
| WO 91/18613 | 12/1991 | WIPO | 252/309 |
| WO 92/02560 | 2/1992 | WIPO | 514/887 |
| WO 93/01798 | 2/1993 | WIPO | 252/312 |
| WO 94/03468 | 2/1994 | WIPO | 424/450 |

OTHER PUBLICATIONS

J.G. Riess, (1991) Fluorocarbon–based in vivo oxygen transport and delivery systems. Vox Sang 61:225–239.

J.G. Riess, (1991) Hemocompatible fluorocarbon emulsions. Blood Compatible Materials and Devices, Chapter 14, 237–270.

T.H. Shaffer, et al., (1992) Liquid Ventilation. Pediatric Pulmonolgy 14:102–109.

T.H. Shaffer, et al., (1994) Perfluorochemical liquid as a respiratory medium. Art, Cells, Blood Subs., and Immob. Biotech. 22(2):315–326.

Kogyo, T. (1982) Magnetic fluid containing carcinostatic agent. Patent Abstracts of Japan 6(202) (C–129) Derwent Publications Ltd., London, GB.

*Primary Examiner*—Thurman K. Page
*Assistant Examiner*—D. Faulkner
*Attorney, Agent, or Firm*—Knobbe, Martens, Olson & Bear, LLP

[57] ABSTRACT

Stable reverse water-in-fluorocarbon emulsions and water-in-fluorocarbon-in-water multiple emulsions comprising the reverse fluorocarbon emulsions. The reverse emulsions comprise a continuous phase which is a highly fluorinated or perfluorinated compound, a discontinuous aqueous phase and a fluorinated surfactant or mixture of surfactants. The multiple emulsions comprise an aqueous continuous phase and a discontinuous phase comprising globules formed of aqueous droplets dispersed into a highly fluorinated or perfluorinated compound. The emulsions can contain pharmacologically active agents, and are particularly suitable for pulmonary drug delivery.

10 Claims, No Drawings

1

STABLE REVERSE AND MULTIPLE FLUOROCARBON EMULSIONS

CLAIM TO FOREIGN PRIORITY

This application claims foreign priority under 35 U.S.C. § 119 to French Application Number 94 07068, filed Jun. 9, 1994.

FIELD OF THE INVENTION

The present invention relates to stable reverse water-in-fluorocarbon emulsions and multiple water-in-fluorocarbon-in-water emulsions comprising the reverse fluorocarbon emulsions. The present invention also relates to the incorporation of drugs into reverse fluorocarbon emulsions, and methods for forming and administering the emulsions.

BACKGROUND OF THE INVENTION

Conventional direct emulsions consist of an oily phase dispersed in the form of droplets in a continuous aqueous phase. Direct fluorocarbon emulsions wherein the fluorocarbon is the oily phase have been used in various biomedical applications. Because of the high oxygen-carrying capacity of fluorocarbons, such fluorocarbon emulsions are particularly useful as blood substitutes to provide oxygen to the vascular system. After introduction of the emulsions, the oxygen dissolved in the dispersed fluorocarbon phase is released into the blood. Other medical uses include the treatment of cardiovascular and cerebrovascular diseases, coronary angioplasty, organ preservation and cancer therapy; diagnostic uses such as nuclear magnetic resonance and ultrasound; and veterinary therapy (Riess J. G., Blood Compatible Materials and Devices": Perspective Towards the 21st Century, Technomics Publishing Co., Lancaster, Pa., Ch. 14, 1991; Riess, J. G., Vox. Sang., 61:225, 1991). Conventional direct fluorocarbon emulsions have been described in, for example, EP-A-0 255 443, FR-A- 2 665 705, FR-A- 2 677 360, FR-A- 2 694 559, FR-A- 2 679 150, WO-A-93 01798, WO90/15807, EP-A-311473 and US 3,975,512.

The pulmonary administration of drugs constitutes a difficult problem because the introduction of drugs directly into the lungs cannot be effectively achieved by means of an aqueous solution. Fluorocarbon direct emulsions wherein the continuous phase is water are unsuitable for pulmonary drug delivery for the same reason.

The use of fluorocarbon liquids for pulmonary ventilation and drug administration via the pulmonary route has been described by Shaffer et al. (Art. Blood Subs. and Cells Immob. Biotech., 22:1994Pediatr. Pulmonol., 14:102, 1992) who contemplated the use of pure fluorocarbon liquids containing a dispersion of drugs in the form of solid powders. These compositions, however, result in non-homogenous, unreliable and irreproducible drug delivery due to the dispersion of the powdered agent in the fluorocarbon phase.

PCT Application No. WO91/18613 describes autoemulsifying "glasses" useful for the generation of reverse or multiple emulsions by contacting the "glass" with an appropriate aqueous phase. This document describes neither fluorinated nor non-fluorinated surfactants. Stable reverse fluorocarbon emulsions capable of effective intrapulmonary drug delivery are not disclosed.

EP-A-0-250 766 describes perfluoropolyether microemulsions of the water-in-oil type to be used as lubricants; these microemulsions contain low amounts of fluorocarbon (ca. 13–30% v/v).

Japanese Patent 57/109714 describes delivery of an anti-cancer agent to a desired site by mixing the agent with a magnetic fluid and applying a magnetic field to the resulting mixture. These fluids may be in the form of direct emulsions, reverse emulsions or multiple emulsions for intravascular administration. Again, this document does not describe stable reverse emulsions suitable for intrapulmonary drug delivery.

Thus, there is a need for stable fluorocarbon emulsions capable of homogeneous, reproducible pulmonary drug delivery in a controlled manner. The present invention satisfies this need.

The same preparations with a fluorocarbon as the continuous phase can be further utilized to deliver drugs and other materials to other body cavities including the gastrointestinal tract, peritoneal cavity, pleural cavity, subarachnoid ventricular spaces, etc.

SUMMARY OF THE INVENTION

One embodiment of the present invention is a stable water-in-oil fluorocarbon emulsion, comprising:

a continuous oily phase comprising 70 to 99.95% (v/v) of at least one highly fluorinated or perfluorinated organic compound;

a discontinuous essentially aqueous phase dispersed in the continuous phase, wherein the amount of aqueous phase is between 0.05 and 30% (v/v) of the emulsion; and a fluorinated surfactant or a mixture of surfactants comprising at least one fluorinated surfactant in the aqueous phase, so that the total amount of surfactant is between 0.01 and 10% (w/v) of the emulsion.

Preferably, the emulsion comprises 80 to 99.95% (v/v) of the continuous oily phase; most preferably, the emulsion comprises 90 to 99.95% (v/v) of the continuous oily phase. In another aspect of this preferred embodiment, the continuous oily phase comprises a highly fluorinated compound such as a linear, branched, cyclic, saturated or unsaturated fluorinated hydrocarbon, optionally containing at least one heteroatom and/or bromine or chlorine atom, wherein at least 30% of the hydrogen atoms of said hydrocarbon compound have been replaced by fluorine atoms. In addition, the emulsion may further comprise at least one organic compound that has a fluorinated region and a hydrogenated region. Advantageously, the fluorinated and hydrogenated compound has the formula $R_F$-W-$R_H$, wherein $R_F$ is a linear, branched or cyclic highly fluorinated radical having from 2 to 14 carbon atoms and optionally contains at least one oxygen atom, at least one halogenated substituent or both;

$R_H$ is a linear, branched, cyclic, saturated or unsaturated hydrocarbon radical, having up to about 18 carbon atoms, optionally containing —O— or —S—; and W is a single bond, or is oxygen or sulfur.

The emulsion may also contain a compound of the formula $R_F$-W-$R_H$, wherein RF is $CF_3$—$(CF_2)_t$ ($1 \leq t \leq 11$); W is a single bond and $R_H$ is an alkyl group having between 1 and 18 carbon atoms.

The fluorinated surfactants useful in forming the emulsions of the present invention contain at least four fluorine atoms. These fluorinated surfactant can be of different types. Classes of fluorinated surfactants contemplated for use in the present invention include, for example, amino acid derivatives, amphiphiles containing phosphorus (e.g., perfluoroalkyl or alkylene mono or dimorpholinophosphate and fluorinated phospholipids) or polyhydroxylated or aminated derivatives. Such fluorinated surfactants are described, for example, in EP-A-0 255 443, FR-A- 2 665 705, FR-A- 2 677 360, FR-A- 2 694 559, FR-A- 2 679 150, PCT/WO90/15807 and EP-A-0311473.

More preferably, the fluorinated surfactant is a (perfluoroalkyl) alkylene dimorpholinophosphate having the formula $R_F$-$R_1$-OP(O) [(N(CH$_2$CH$_2$)$_2$ O]$_2$, wherein $R_F$ is a linear, branched or cyclic highly fluorinated radical having from 2 to 12 carbon atoms and optionally contains at least one oxygen atom, at least one Cl or Br, and $R_1$ is a saturated or unsaturated, linear or branched hydrocarbon, optionally containing at least one oxygen atom, one sulfur atom or both. According to another aspect of this embodiment, the fluorinated surfactant is a (perfluoroalkyl) alkylene mono- ordimorpholinophosphate, preferably 5-(perfluorooctyl) pentyl dimorpholinophosphate, 2-(perfluorooctyl)undecyl dimorpholinophosphate or 11-(perfluorooctyl)undecyl dimorpholinophosphate. Alternatively, the emulsion may contain at least one fluorinated surfactant and at least one hydrogenated surfactant. Preferably, the hydrogenated surfactant is a phospholipid, polyoxyethylene polyoxypropylene-type copolymer or polyoxyethylenic sorbitan ester.

In addition, the emulsion may further comprise one or more of the following additives: mineral salts, buffer agents, solvents and dispersing agents, oncotic and osmotic agents, nutritive agents, hydrophilic or lipophilic pharmacologically active substances; and wherein the substances are present in the aqueous phase, the oily phase, at the interface between the phases; or in both of the phases. Preferably, the additive is a water-soluble or water-dispersible pharmacologically active substance; most preferably, the pharmacologically active substance is an antibiotic, tuberculostatic antimycobacterial, anticancer agent, pulmonary vasoactive substance, mucolytic agent, antiviral agent, pharmaceutically active peptide, nucleic acid, genetic material, immunoactive agent or surfactant. The pulmonary vasoactive substance may be a pulmonary vasoactive bronchodilator or respiratory stimulant.

Another embodiment of the present invention is a process for the preparation of a reverse water-in-fluorocarbon emulsion comprising the following steps:

a) solubilizing or dispersing a fluorinated surfactant or a mixture of surfactants comprising at least one fluorinated surfactant in a highly fluorinated or perfluorinated continuous phase;

b) adding an aqueous phase optionally containing one or more dispersing agents or additives to the continuous phase product of step (a) to form a mixture of fluorocarbon and aqueous phase; and (c) emulsifying the mixture of step (b) to form the reverse water-in-fluorocarbon emulsion.

The method may further comprise the step of sterilizing the reverse emulsion by heat treatment or filtration. Preferably, the emulsifying step (c) is effected by mechanical homogenization.

The present invention also provides multiple water-in-fluorocarbon-in-water emulsions comprising the reverse emulsion described hereinabove and an aqueous phase in which at least one surfactant is dispersed.

Furthermore the internal aqueous compartment of either the reverse or the multiple emulsions can contain micelles, vesicles or other colloidal aggregates that can, among others, achieve further compartimentalization of this internal space.

The present invention also provides a multiple emulsion as described above, wherein the continuous oily phase further comprises at least one organic compound that has a fluorinated region and a hydrogenated region. Preferably, the multiple emulsion contains a compound of the formula $R_F$-W-$R_H$, wherein $R_F$ is CF$_3$—(CF$_2$)$_t$ (1≦t≦1); W is a single bond and $R_H$ is a saturated or unsaturated alkyl group having between 1 and 18 carbon atoms. In another aspect of this preferred embodiment, the fluorinated surfactant is a (perfluoroalkyl) alkylene dimorpholinophosphate having the formula $R_F$-$R_1$-OP(O) [(N(CH$_2$CH$_2$)$_2$O]$_2$, wherein $R_F$ is a linear, branched or cyclic highly fluorinated radical having from 2 to 12 carbon atoms and optionally contains at least one oxygen atom, at least one halogenated substituent selected from the group consisting of Cl and Br, and $R_1$ is a saturated or unsaturated, linear or branched hydrocarbon, optionally containing at least one oxygen atom, one sulfur atom or both. Advantageously, the multiple emulsion contains at least one fluorinated surfactant and at least one hydrogenated surfactant. Advantageously, the hydrogenated surfactant is either a phospholipid, polyoxyethylene polyoxypropylene type copolymer or polyoxyethylenic sorbitan ester. Further, the fluorinated surfactant may be a perfluoroalkylphosphatidylcholine or perfluoroalkylamine oxide. Preferably, the fluorinated surfactant is a (perfluoroalkyl) alkylene mono- or dimorpholinophosphate; more preferably, the fluorinated surfactant is 11-(perfluorooctyl)undecyl dimorpholinophosphate or 2-(perfluorooctyl)ethyl dimorpholinophosphate. further, the multiple emulsion may further comprise one or more of the following additives: mineral salts, solvents and dispersants, buffer agents, oncotic and osmotic agents, nutritive agents, hydrophilic or lipophilic pharmacologically active substances; and wherein the substances are present in either the internal or in the external aqueous phases, the oily phase, at the interface between the phases; or in any of the phases. Preferably, the additive is a hydrophilic or lipophilic pharmacologically active substance. According to another aspect of this preferred embodiment, the pharmacologically active substance is an antibiotic, tuberculostatic, antimycobacterial, anticancer agent, pulmonary vasoactive substance, mucolytic agent, antiviral agent, genetic material, immunoactive agent or surfactant.

Another embodiment of the invention is a process for the preparation of a multiple water-in-fluorocarbon-in-water emulsions comprising the following steps:

a) solubilizing or dispersing a fluorinated surfactant or a mixture of surfactants comprising at least one fluorinated surfactant in a highly fluorinated or perfluorinated continuous phase;

b) adding an aqueous phase optionally containing one or more co-solvents, dispersing agents and active additives additives to the continuous phase product of step (a) to form a mixture of fluorocarbon and aqueous phase;

(c) emulsifying the mixture of step (b) to form the reverse water-in-fluorocarbon emulsion;

(d) adding said reverse emulsion to an aqueous solution or dispersion containing a fluorinated or non-flourinated surfactant and optionally other additives including active substances; and (e) emulsifying the mixture of step (d) to obtain the multiple water-in-fluorocarbon-in-water emulsion.

The present invention also provides a method for adjusting the concentration of the active agents comprising diluting any of the multiple emulsions described above in water or an aqueous media or a polar solvent. Preferably, the internal aqueous compartment contains micelles, vesicles or other colloidal aggregates.

DETAILED DESCRIPTION OF THE INVENTION

The present invention provides stable reverse emulsions comprising a continuous fluorocarbon phase into which are dispersed droplets of aqueous phase. Said reverse emulsions may contain hydrophilic or lipophilic drugs and thereby constitute a vehicle for drug administration through the pulmonary route and other routes. The method of drug administration using the reverse fluorocarbon emulsions of the invention therefore constitutes an important step forward, because it provides a way to produce a homogenous dispersion of a drug in the lungs and other bodies cavities and controlled release of the drug over time.

The highly fluorinated or perfluorinated organic compounds comprising the continuous fluorocarbon phase are chosen for their low toxicity, surface tension and spreading coefficient. The use of a fluorinated surfactant, or of a mixture of surfactants comprising at least one fluorinated surfactant allows the formation of stable reverse emulsions.

According to the invention, the stable reverse fluorocarbon emulsion comprises from 70 to 99.95% (v/v) of an oily continuous phase made up of a highly fluorinated or perfluorinated organic compound; from 0.05 to 30% (v/v) of an aqueous phase dispersed in the form of droplets in the continuous oily phase; and from 0.01 to 10% (w/v) of a fluorinated surfactant or a mixture of surfactants comprising at least one fluorinated surfactant. The volume percentages of the aqueous phase and of the oily fluorocarbon phase comprise the surfactant or surfactants they contain.

In preferred embodiments, the reverse emulsions of the invention contain from 80 to 99.95*i (v/v), and more preferably from 90 to 99.95% (v/v) of continuous oily phase.

The highly fluorinated or perfluorinated compounds may be linear, branched or cyclic, saturated or unsaturated fluorinated hydrocarbons. The invention also includes the use of conventional structural derivatives of these compounds, as well. In addition, these totally or partially fluorinated compounds may contain one or more heteroatoms and/or atoms of bromine or chlorine. The term "partially fluorinated" indicates that at least 30% of the hydrogen atoms in the hydrocarbon or derivative thereof have been replaced with fluorine atoms. Generally, these hydrocarbons comprise from 6 to 16 carbon atoms. Such fluorinated compounds include, but are not limited to, linear, cyclic or polycyclic perfluoroalkanes, perfluoroalkenes, perfluoroamines and perfluoroalkyl bromides. These compounds may be used either alone or in combination. In a preferred embodiment of the invention the fluorinated compound consists of perfluorooctyl bromide, $C_8F_{17}Br$ (PFOB) or of perfluorooctylethane $C_8F_{17}C_2H_5$ (PFOE).

In addition, the continuous fluorocarbon phase may also include a compound having at least one fluorinated region and at least one other hydrogenated region, for example, a compound of the formula $R_{F-W-RH}$, in which $R_F$ is a linear, branched or cyclic highly fluorinated radical having from about 2 to about 14 carbon atoms and optionally including at least one oxygen atom and/or at least one halogenated substituent; $R_H$ is a linear, branched or cyclic saturated or unsaturated hydrocarbon radical having up to about 18 carbon atoms, optionally containing at least one—O—or—S—group; and W is a single bond, oxygen or sulfur. In one preferred embodiment, in the fluorinated and hydrogenated compounds of the invention, $R_F$ is $CF_3(CF_2)_t$, wherein t is from 1 to 11; W is absent and replaced by a single bond, and $R_H$ is a saturated or unsaturated alkyl group of from 1 to 18 atoms.

In another preferred embodiment, the fluorinated surfactants useful in forming the emulsions of the present invention generally contain at least four fluorine atoms. These fluorinated surfactant can be of different types. Classes of fluorinated surfactants contemplated for use in the present invention include, for example, amino acid derivatives, amphiphiles containing phosphorus (e.g., (perfluoroalkyl) alkylene mono or dimorpholinophosphate and fluorinated phospholipids) or polyhydroxylated or aminated derivatives including amine oxides. Such fluorinated surfactants are described, for example, in EP-A-0 255 443, FR-A- 2 665 705, FR-A- 2 677 360, FR-A- 2 694 559, FR-A- 2 679 150, WO90/15807 U.S. Pat No. 3,828,085 and EP-A-0311473.

In a particularly preferred embodiment, the reverse emulsions of the invention contain the (perfluoroalkyl)alkylene surfactant of the formula:

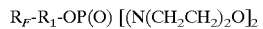

$R_F-R_1-OP(O) [(N(CH_2CH_2)_2O]_2$ wherein $R_F$ is as previously described and $R_1$ is a saturated or unsaturated, linear or branched hydrocarbon chain which may contain at least one oxygen and/or sulfur atom.

The fluorinated surfactants may also be associated with hydrogenated, non-ionic, anionic, cationic or zwitterionic surfactants. Such hydrogenated surfactants include, for example, phospholipids, copolymers of the polyoxyethylene polyoxypropylene type (e.g., Pluronic F-68®) and polyoxyethylene sorbitan esters.

The reverse emulsions of the invention may also comprise one or more additives which are present either in the dispersed aqueous phase in the form of droplets, or in the fluorocarbon phase, in both of these phases, or at the interface between the phases. The additives may include, for example, mineral salts, buffers, oncotic and osmotic agents, nutritive agents, active principles, pharmaceutically active substances, nucleic acids, genetic material, immunoactive agents or any other ingredient capable of augmenting the favorable characteristics of the reverse emulsions including their stability, therapeutic efficacy and tolerance.

In a preferred embodiment, a pharmaceutical preparation for the pulmonary administration of drugs is provided which comprises a pharmacologically active substance dispersed in the aqueous phase of the reverse emulsion. Examples of appropriate pharmacologically active substances are antibiotics such as gentamicin, erythromycin and doxycycline; tuberculostatic antimycobacterials such as pyrazinamide, ethambutol and isoniazid; anticancerous substances such as cisplatinum, cyclophosphamide, 5-fluorouracil and doxorubicin; pulmonary vasoactive substances and regulators of pulmonary hypertension such as tolazoline; respiratory stimulants such as doxapram; vasoactive bronchodilators such as epinephrine and theophylline; mucolytic agents such as acetylcysteine; antiviral agents such as ribavirin; and surfactants such as dipalmitoylphosphatidylcholine.

The reverse emulsions of the invention are generally prepared by solubilizing or dispersing the fluorinated surfactant or mixture of surfactants in the fluorocarbon phase by mechanical stirring; adding the appropriate quantity of aqueous phase which can contain one or more surfactants, dispersant agents or additives to the fluorocarbon phase; and emulsifying the mixture by conventional homogenization such as, for example, microfluidization, sonication or homogenization under pressure. In certain situations, reverse emulsions having a low water content may be prepared using a fluorinated surfactant with only simple stirring; no high pressure homogenization is necessary.

The reverse emulsions of the invention may be sterilized, for example, by autoclaving at 121° C. for 15 minutes or by filtration through a 0.22 $\mu$m filter.

These reverse emulsions can also conveniently be diluted in a fluorocarbon very easily to adjust dosage and administration regimen.

The reverse emulsions may also be dispersed in the form of fluorocarbon globules inside a second continuous aqueous phase, each globule containing droplets of dispersed first aqueous phase. Such a multiple emulsion may be prepared by addition of a reverse emulsion to an aqueous phase in which is dispersed at least one fluorinated or non-fluorinated surfactant described hereinabove. The amount of surfactant employed in the formation of multiple emulsions will depend on the quantity of aqueous phase and reverse emulsion used. In general, for an aqueous phase constituting 50% to 99.95% (v/v) of a reverse emulsion, the amount of surfactant used is between about 0.01 and about 10% (w/v) of the aqueous phase. The second continuous phase can also contain polar solvents including for example glycol, glycerol, dimethylformamide or dimethylsulfoxide as well as additives selected from the group consisting of mineral salts, buffer agents, oncotic and osmotic agents, nutritive agents, hydrophilic or lipophilic pharmacologically active substances; and wherein the substances are present in the aqueous phase, the oily phase, at the interface between the phases; or in both of the phases.

The internal aqueous compartment of either the reverse or the multiple emulsion can also contain micelles, vesicles or other colloidal aggregates in view of further contributing to control the entrapment and release of active material.

Preparation of the reverse fluorocarbon emulsions of the present invention is described in the following examples.

The volume percentages of the aqueous phase and of the oily fluorocarbon phase comprise the surfactant or surfactants they contain.

EXAMPLE 1

PFOB (95% v/v), water (506% v/v), F8C11DMP (0.6% w/v), High-pressure homogenization, Rannie 11-(F-octyl)undecyl dimorpholinophosphate (F8C11DMP; $(C_8F_{17}C_{11}H_{22}OP(O)[(N(CH_2CH_2)_2O]_2$ (0.60 g) was dispersed in perfluorooctyl bromide (PFOB) (95 mL, 182.4 g) by mechanical stirring (Ultra-Turrax T25 IKA, 5 min). Purified water (5 mL) was added dropwise to the fluorocarbon phase with stirring. The mixture was then pre-emulsified by mechanical stirring (Ultra-Turrax, 5 min). The pre-emulsion thus obtained was homogenized under high pressure (Rannie Mini-Lab 8.30H, APV Rannie, 15 min, 5000–8000 psi). The resulting reverse emulsion was very fluid and opalescent. The average particle size measured immediately after preparation was 600±350 nm (laser light scattering). After 4 days, the average particle size was 2±0.2 $\mu$m as assessed by centrifugal sedimentation. No significant further variation in size was observed during 1 month of storage at 4° C. or at 25° C.

EXAMPLE 2

PFOB (95% v/v), water (5% v/v), F8C2DMP (0.6% w/v), Sonication 2-(F-octyl)ethyl dimorpholinophosphate (F8C2DMP; $C_8F_{17}C_2H_4OP(O)[(N(CH_2CH_2)_2O]_2$ (0.15 g) was placed in a Rosette cell and dispersed in PFOB (23.75 mL, 45.6 g) by mechanical stirring (Ultra-Turrax, 2 min). Purified water (1.25 mL) was added to the fluorocarbon phase. The mixture was then emulsified by sonication (Branson B30, titanium probe, 3mm diameter, power 4, pulsed mode at 50%, 10 min, 0–5° C.). The resulting reverse emulsion was very fluid, whitish in color, with an average particle size of 0.3 $\mu$m (centrifugal sedimentation). The reverse character of the emulsion was verified by phase contrast microscopy after addition of methylene blue. The average droplet size in the emulsion was about 1 $\mu$m after 3 months of storage at 25° C.

EXAMPLE 3

PFOB (97% v/v), water (3% v/v), F8C11DMP, 0.6% w/v), High pressure homogenization. Emulsiflex-B3®

F8C11DMP (0.012 g) was dispersed in PFOB (1.94 mL) by mechanical stirring (Ultra-Turrax T25 IKA, 1 min). Purified water (0.06 mL) was added dropwise to the fluorocarbon phase while stirring. The mixture was then pre-emulsified by mechanical stirring (Ultra-Turrax, 5 min). The pre-emulsion thus obtained was homogenized under high pressure (Emulsiflex-B3, 8000 psi, 3-7 passes). The resulting reverse emulsion was fluid and opalescent. No phase separation was observed after one month of storage at 25° C.

EXAMPLE 4

PFOB (99.8% v/v). water (0.2% v/v) and F8C2DMP (0.6% w/v). Dispersion without mechanical stirring F8C2DMP (0.15 g) was hydrated with purified water (0.05 mL) for 1 hour. The mixture was then dispersed in PFOB (24.95 mL, 47.9 g), resulting in a translucent dispersion having a continuous fluorocarbon phase. No mechanical emulsification or sonication was employed. The average size of the droplets of water measured after emulsion preparation was about 100 nm (laser light scattering). No change in size was observed after 1 month of storage at 25° C.

Examples of reverse emulsions using different formulations are detailed in Table I. The emulsions described in Examples 5–9 were prepared by sonication according to Example 2. The emulsions described in Examples 10–17 were prepared by high pressure homogeneization (Emulsiflex-B3) according to Example 3.

The results generated in Examples 5 –17 are summarized in Table 1.

TABLE 1

| Example | Fluorocarbon (% v/v) V in mL | Water (% v/v) V in mL | Surfactant (% w/v) Weight in g | Other component of aqueous phase (% w/v) weight in g | Emulsion aspect (initial mean diameter in microns) | Stability of the emulsion at 25° C., Time, mean diameter in microns |
|---|---|---|---|---|---|---|
| 5 | PFOB (95) 23.75 | (5) 1.25 | F8C2DMP (0.6) 0.15 | EYP (1) 0.25 | (0.4) | 3 months, 0.7 |
| 6 | PFOE (95) 23.75 | (5) 1.25 | F8C2DMP (0.6) 0.15 | F7AO (1) 0.25 | fluid, whitish (0.45) | 1 month, 0.55 |
| 7 | PFOE (95) 23.75 | (5) 1.25 | F8C2DMP (0.6) 0.15 | Pluronic-F68 (1) 0.25 | (0.55) | 3 months, 0.65 |
| 8 | PFOB* (60) 15 | (10) 2.5 | F8C2DMP (0.6) 0.15 | — | <1 micron | — |
| 9 | PFOB (97) 1.94 | (3) 0.6 | F8C5DMP (0.6) 0.013 | — | fluid, whitish | No phase separation after 1 month |
| 10 | PFOB (95) 2.85 | (5) 0.15 | F8C11DMP (0.6) 0.018 | NaCl 0.125 | fluid, bluish transparent (30 ± 10 nm) | No phase separation after 1 month |
| 11 | PFOB (70) 1.4 | (30) 0.6 | F8C11DMP (5) 0.1 | — | fluid, milky | No phase separation after 1 month |
| 12 | PFOB (97) 1.94 | (3) 0.06 | F8C11DMP (0.6) 0.012 | NaCl 0.125 | fluid, bluish | No phase separation after 1 month |
| 13 | PFOB (70) 1.4 | (30) 0.6 | F8C11DMP (.5) 0.1 | NaCl 0.125 | fluid, bluish | No phase separation after 1 month |
| 14 | PFOB (97) 1.94 | (3) 0.06 | F8C11DMP (0.6) 0.012 | $CaCl_2$ 0.125 | fluid, bluish | No phase separation after 1 month |
| 15 | PFOB (97) 1.94 | (3) 0.06 | F8C11DMP (0.6) 0.012 | KI 0.125 | fluid, bluish | No phase separation after 1 month |
| 16 | PFOB (97) 1.94 | (3) 0.06 | F8C11DMP (0.6) 0.012 | D-glucose 0.125 | fluid, bluish | No phase separation after 1 month |
| 17 | PFOB (97) 1.94 | (3) 0.06 | F8C11DMP (0.6) 0.012 | Pluronic-P85 ® 0.125 | fluid, bluish | No phase separation after 1 month |

*This reverse emulsion also contains 30% of a fluorocarbon/hydrocarbon compound ($C_6F_{13}C_{10}H_{21}$, F6H10, 7.5 mL).
PFOB: perfuorooctyl bromide; PFOE: perfluorooctylethane; F8C2DMP: 2-(perfluorooctyl)ethyl dimorpholinophosphate; F8C11DMP: 11-(perfluorooctyl)undecyl dimorpholinophosphate; EYP; egg yolk phospholipid; F7AO; pentadecafluoroheptylamidopropyl-dimethylamine oxide.

EXAMPLE 18

PFOB (97% v/v), water (3% v/v), F8C11DMP 0.6% w/v), acetylcholine chloride (0.125% w/v), High pressure homogenization F8C11DMP (0.012 g) was dispersed in PFOB (1.94 mL) by mechanical stirring as in Example 11. Purified water (0.6 mL) containing acetylcholine chloride at 0.125% w/v was added dropwise to the fluorocarbon phase while stirring. The mixture was then pre-emulsified and emulsified as in Example 3. The resulting reverse emulsion was fluid and bluish. No phase separation was observed after at least one month of storage at 25° C.

EXAMPLE 19

PFOB (95% v/v), water (5% v/v), F8C11DMP (0.6% w/v), and pyrazinamide (0.05% w/v). High-pressure homogenization Pyrazinamide (0.05 g) was solubilized in purified water (5 mL). The method described in Example 1 was then followed. The quantities of PFOB, F8C11DMP, as well as the emulsification conditions were identical to those used in Example 1. The resulting reverse emulsion was transparent and bluish. The average droplet size measured immediately after preparation was 40±35 nm (laser light scattering). The emulsion was stable, with no detectable change in particle size for at least 1 week at 4° C. or at 25° C.

EXAMPLE 20

PFOE (95% v/v) water (5% v/v), F8C2DMP (0.6% w/v) Pluronic-F68®(1% w/v), epinephrine (0.02% w/v)

F8C2DMP (0.15 g) was dispersed in PFOE (23.75 mL, 45.6 g) by mechanical stirring (3 min). Pluronic-F68 (0.25 g) and epinephrine (5 mg) were then co-dispersed in purified water (1.25 mL) by mechanical stirring. This dispersion was added to the fluorocarbon phase. The mixture was emulsified by sonication following the protocol described in Example 2. The resulting reverse emulsion had an average particle size of 0.60 µm (centrifugal sedimentation). After 3 months of storage at 25° C., the average particle size was 0.80 µm.

EXAMPLE 21

PFOE (70% v/v), F4H8E (20% v/v), F6H10 (5% v/v), water (5% v/v), F8C11DMP (1% w/v), prednisone (0.02% w/v)

The steroidal adrenocortical anti-inflammatory drug prednisone (0.02% w/v) was dissolved in perfluorobutyl-1-decene ($C_4F_9CH=CHC_8H_{17}$); F4H8E; 2 mL) by gentle heating and stirring. Perfluorohexyldecane ($C_6F_{13}C_{10}H_{21}$; F6H10;0.5 mL) was then added, followed by perfluorooctylethane ($C_8F_{17}C_2H_5$; PFOE; 7 mL) at room temperature, and followed by F8C11DMP (0.5 g). Water (0.5 mL) was added to this solution while stirring with an Ultra-Turrax. The mixture was emulsified by sonication following the protocol described in Example 2 to yield the whitish prednisone-containing reverse emulsion.

EXAMPLE 22

Biological tolerance of reverse emulsions

The reverse emulsion described in Example 7 was intraperitoneally injected into 10 mice (12.5 mL/kg per animal). After one month, all of the animals were alive. No perturbation in their behavior or their growth was observed during this period.

Examples 23 and 24 describe the preparation of multiple water-in-fluorocarbon-in-water emulsions containing a fluorinated surfactant.

EXAMPLE 23

PFOB (45% v/v)/water (55% v/v), F8C2DMP (0.6% w/v) and egg-yolk phospholipids (1% w/v)

F8C2DMP (0.3 g) was dispersed in PFOB (22.5 mL, 43.2 g) by mechanical stirring (5 min). Purified water (2.5 mL) was added to the fluorocarbon phase. Emulsification was achieved by sonication as described in Example 2. A reverse water-in-fluorocarbon emulsion was obtained. This reverse emulsion (10 mL) was added dropwise to an aqueous dispersion of egg-yolk phospholipids (0.2 g in 10 mL of purified water). A milky emulsion was obtained. Optical microscopy revealed fine droplets inside larger globules dispersed in a continuous phase. The methylene blue test (coloring of the fine droplets and of the continuous phase) showed that the emulsion was a triple water/fluorocarbon/water emulsion. The average size of the fluorocarbon globules was about 8–10 μm and that of the water droplets <1μm. No modification in the size of the fluorocarbon globules was observed after heat-sterilization (121° C., 15 min, $10^5$ $Nm^{-2}$) and after one month of storage at 25° C.

EXAMPLE 24

PFOB (47.5% v/v)/water (52.5% v/v), F8C11DMP (0.3% w/v) and egg-yolk phospholipids (1% w/v)

A reverse emulsion prepared as described in Example 1 (1 mL) was added dropwise to 1 mL of an aqueous dispersion containing 10 mg of natural phospholipids with mechanical stirring. A milky water-in-fluorocarbon-in-water emulsion was obtained. The methylene blue test showed that the continuous phase was aqueous.

What is claimed is:

1. A stable water-in-oil fluorocarbon emulsion, comprising:
    a continuous oily phase comprising 70–99.5% (v/v) of at least one highly fluorinated or perfluorinated organic compound;
    a discontinuous aqueous phase dispersed in the continuous phase, wherein the amount of aqueous phase is between 0.05 and 30% (v/v) of the emulsion; and
    a fluorinated surfactant or a mixture of surfactants comprising at least one fluorinated surfactant,
    wherein the total amount of surfactant is between 0.01 and 10% (w/v) of the emulsion and
    wherein the reverse emulsion is a multiple water-in-fluorocarbon-in-water emulsion in an aqueous phase in which at least one surfactant is dispersed.

2. A multiple emulsion according to claim 1, wherein the continuous oily phase further comprises at least one organic compound that has a fluorophilic region and a nonfluorophilic hydrophobic region.

3. A multiple emulsion according to claim 2 containing a compound of the formula $R_F$-W-$R_H$, wherein $R_F$ is $CF_3$—$(CF_2)_t$ ($1 \leq t \leq 11$); W is a single bond and $R_H$ is a saturated or unsaturated alkyl group having between 1 and 18 carbon atoms.

4. A multiple water-in-fluorocarbon-in-water emulsion according to claim 6, wherein the fluorinated surfactant is a (perfluoroalkyl)alkylene dimorpholinophosphate having the formula $R_F$-$R_1$-OP(O) $[(N(CH_2CH_2)_2O]_2$, wherein $R_F$ is a linear, branched or cyclic highly fluorinated radical having from 2 to 12 carbon atoms and optionally contains at least one oxygen atom and/or at least one halogenated substituent selected from the group consisting of Cl and Br, or both, and $R_1$ is a saturated or unsaturated, linear or branched hydrocarbon, optionally containing at least one oxygen atom, and/or at least one sulfur atom.

5. A multiple emulsion according to claim 1 containing at least one fluorinated surfactant and at least one hydrogenated surfactant.

6. A multiple emulsion according to claim 5, wherein the hydrogenated surfactant is selected from the group consisting of phospholipids, polyoxyethylenepolyoxypropylene type copolymers and polyoxyethylenic sorbitan esters.

7. A multiple emulsion according to claim 5, wherein the fluorinated surfactant is selected from the group consisting of perfluoroalkylphosphatidylcholines and perfluoroalkylamine oxides.

8. A multiple emulsion according to claim 5, wherein the fluorinated surfactant is a (perfluoroalkyl)alkyl or alkylene mono- or dimorpholinophosphate.

9. A multiple emulsion according to claim 8, wherein the fluorinated surfactant is 11-(perfluorooctyl)undecyl dimorpholinophosphate.

10. A multiple emulsion according to claim 8, wherein the fluorinated surfactant is 2-(perfluorooctyl)ethyl dimorpholinophosphate.

* * * * *

UNITED STATES PATENT AND TRADEMARK OFFICE
CERTIFICATE OF CORRECTION

PATENT NO. : 5,904,933
DATED      : May 18, 1999
INVENTOR(S) : Jean G. Reiss, Marie-Pierre Kraft It is certified that error appears in the above-identified patent and that said Letters Patent is hereby corrected as shown below:

Claim 4, column 12, line 30, please change "claim 6" to --claim 1--.

Signed and Sealed this

Twenty-third Day of May, 2000

Attest:

Q. TODD DICKINSON

*Attesting Officer*       *Director of Patents and Trademarks*